United States Patent [19]
Krall et al.

[11] Patent Number: 5,976,562
[45] Date of Patent: *Nov. 2, 1999

[54] PROCESS FOR PRODUCING BACTERICIDAL/FUNGICIDAL PLASTIC BODIES

[76] Inventors: Theodor Krall, Rosenu 7a, A6600 Lechaschau, Austria; J. Peter Guggenbichler, Hebelstrasse 4, D-90491 Nürnberg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/663,161

[22] PCT Filed: Feb. 1, 1995

[86] PCT No.: PCT/DE95/00122

§ 371 Date: Oct. 2, 1996

§ 102(e) Date: Oct. 2, 1996

[87] PCT Pub. No.: WO95/20878

PCT Pub. Date: Aug. 10, 1995

[30] Foreign Application Priority Data

Feb. 1, 1994 [DE] Germany ............... 44 03 016
Aug. 5, 1994 [DE] Germany ............... 44 27 829

[51] Int. Cl.$^6$ .................................. A01N 25/34
[52] U.S. Cl. ................. 424/402; 424/404; 523/122
[58] Field of Search .................. 424/402, 404; 523/122; 264/140, 141, 143; 427/2.1, 250, 289, 357; 241/24.25, 24.28

[56] References Cited

U.S. PATENT DOCUMENTS

| | | | |
|---|---|---|---|
| 5,180,585 | 1/1993 | Jacobson et al. | 424/405 |
| 5,236,649 | 8/1993 | Hall et al. | 264/130 |
| 5,418,056 | 5/1995 | Noguchi et al. | 428/323 |
| 5,538,766 | 7/1996 | Banks et al. | 427/585 |

*Primary Examiner*—S. Mark Clardy
*Assistant Examiner*—Kathryne E. Shelborne
*Attorney, Agent, or Firm*—Akin, Gump, Strauss, Hauer & Feld, L.L.P.

[57] ABSTRACT

Objects for use in medical application that are produced from plastics required to have an antimicrobially effective content of metals (or metal compounds) can be produced inexpensively by coating a plastic blank in the form of film, granules or fibers with the desired metal (or metal compound) according to the methods used in thin-film technology. The thus obtained intermediate is subsequently comminuted and mixed and, as the starting product for the desired final form, further processed. As a result, these objects are antimicrobially effective on every area of their surface, i.e. also on internal surfaces. The amount necessary for full effectiveness of the antimicrobially active substances, which in the case of the subject-matter of this invention are oligodynamically active metals (or metal compounds), is only a small percentage of that necessary when they are introduced into the plastic in the form of powder, which fact results in considerable financial advantages.

18 Claims, No Drawings

PROCESS FOR PRODUCING BACTERICIDAL/FUNGICIDAL PLASTIC BODIES

FIELD OF THE INVENTION

This invention relates to processes for producing plastic bodies that can be further processed, particularly for use in the medical field, and exhibit an antimicrobially effective content of metals or metal compounds (in the following called active agents).

BACKGROUND OF THE INVENTION

These are especially materials and/or compounds thereof whose oligodynamical effect is known, such as silver, copper and gold, but also other heavy metals such as zinc and also lanthanides that have an effect on bacteria and/or fungi as desired according to this invention, i.e. they eliminate them, they prevent them from multiplying as well as from sticking to or embedding themselves in the plastic, or at least largely keep them from doing so.

A look at the present situation on the market shows that pre-products or finished parts made of such plastics are not yet commercially available, but according to the state of the art they can indeed be produced to function.

One reason why these products have not yet been introduced on the market to a considerable extent, is most likely the question of time and/or energy and thus costs involved in the production of such plastics.

On the one hand, this holds true for the costs of the amounts of metal and/or metal compound necessary for the desired purpose, in particular of silver, when these substances are to be included in the plastic in the powder form, in which case the lower limit for the metal and/or metal compound to be effective is frequently stated to be in an order of magnitude of 1 wt. % of the plastic; however, larger amounts are always stated to be even more effective. In this context, reference is made to the patent publications U.S. Pat. No. 4,054,139, WO-A-84/01721, EP-A-0 190 504, DE-A-37 25 728, EP-A-0 251 783 and DE-A-39 42 112.

On the other hand, this holds true for the costs of the actually rather elaborate wet process for the treatment of plastics, e.g. according to DE-C-42 26 810, which correspondingly is only to be used in special cases and in which very small amounts of the active agent are sufficient.

Another way of avoiding the high material costs for antimicrobial finishing is not to subject the plastic as a whole to antimicrobial finishing but to coat the finished objects produced from this plastic with active agents.

However, all physical methods (such as vapor deposition, cathodic sputtering, plasma-assisted vapor deposition, ionic plating, ion implantation) and also the chemical methods (e.g. currentless electro-plating, reactive vapor deposition, reactive cathodic sputtering, CVD, PACVD) work such that only the surfaces facing the source of the active substance to be applied or, e.g. in the case of plasma-assisted methods, at least only the surfaces openly facing the environment are coated. The internal surfaces of objects, which are usually particularly important for medical applications, e.g. the internal surfaces of catheters, however, cannot be reached by the aforementioned methods and thus remain uncoated.

SUMMARY OF THE INVENTION

The problem underlying the present invention is thus to provide a method for producing oligodynamically active plastic bodies not exhibiting the aforementioned disadvantages, i.e. that are easy to produce, require only small amounts of oligodynamical metal and/or the compound(s) thereof and uniformly act on all surfaces, also on those that are hard to get to.

This problem is solved by a method for producing plastic bodies having a content of one or several oligodynamically active metal(s) or metal compounds as an active substance, characterized in that the active substance is embedded in the plastic in the form of discrete particles, wherein the amount of active substance is no more than 1.0 wt. %, preferably no more than 0.5 wt. %, based on the total weight of the plastic body, and the maximum size of the discrete active substance particles is less than 500 nm.

Active substances in powder form of any kind that are easy to handle are only produced and for sale with finenesses of grain up to the micron range (i.e. $\geq 1$ μm) and sub-micron range (i.e. $>0.1$ μm). According to the manufacturer's information, the thus achieved specific surface, for instance in the case of the finest commercially available silver powder having a rated grain size of 2–3.5 μm, which of course comprises also a certain portion of coarser particles and sub-micron particles, which is unavoidable, amounts to 0.5 to 1 $m^2/g$. Other frequently used and also less expensive silver powders have even larger particles and correspondingly lower specific surfaces.

Even finer, colloidal preparations can generally only be prepared as sols or gels. The thus present portion of protective colloid during further processing and use usually involves considerable undesired side effects. Besides, such colloidal preparations are often rather unstable and, in addition, often relatively expensive.

In the process of this invention, plastic bodies are therefore preferably produced such that the blank is coated with the bactericidally and/or fungicidally (oligodynamically) active substance by means of a chemical or physical process, the obtained blank (pre-product) is comminuted and/or molten down, from which mass the desired plastic body is then produced according to common methods.

DETAILED DESCRIPTION OF PREFERRED EMBODIMENTS

Very thin and, depending on the process, fine and even extraordinarily fine structures of the deposited material can be achieved by means of physical and chemical methods for coating surfaces, which structures correspond to or at least come close to the fineness of colloidal preparations. This holds true especially when the deposited layers are very thin.

The resulting minimum value of the specific surface is 19 $m^2/g$ for such coatings, for instance just by mathematic calculation of the outer geometry at a layer thickness of 10 nm e.g. for the deposition of silver. Preferably the layer thickness is 1 to 50 nm.

If also those surfaces are taken into account that arise perpendicular to the main surface due to open laying grain edges and due to fracturing of the surface due to errors in the uniformity of the deposition, the resulting value for the specific surface is even higher in practice.

Preferably, the maximum particle size distribution of the active substance is below 100 nm in at least one dimension (e.g. in particles present in the form of flocks or flakes), more preferably 10 nm. In thin layers, the grain size may even be smaller than 1 nm.

Crystalline materials (PTFE, some polyimides) must e.g. be comminuted by grinding; remelting is not possible (in practice). They are then shaped as desired by e.g. (pressure) sintering.

Tests showed that plastics having principally a low but most finely dispersed content of metal particles (or particles of metal compounds) with a correspondingly large specific active surface have the same effect as plastics having a considerably higher but less finely dispersed content of metals (or metal compounds) with a correspondingly smaller specific active surface.

Since, however, the supply of these active substances, which is decisive for their long-term effect, is undoubtedly larger when the particles are coarser, it can be mentioned as another advantage of the plastics produced according to the above-mentioned method that for particularly critical cases these plastics may be equipped with metal (or metal compounds) having particles whose size may be influenced for an optimum long-term effect from the very beginning by a suitable process for the production of the layer.

The coating can take place on film (see Example), which can then be re-comminuted and further processed. It may also be applied to fibers or granules with the same end result of the production of the desired final concentration of the active substance in the plastic.

Plastic blanks that already contain fillers may also be used. Preferred are plastic blanks whose fillers do not considerably alter the chemical and physiological properties of the plastic used as a pre-product. Preferred fillers are those that result in the end products produced therefrom being easily recognizable by means of X-rays and/or having an increased specific weight (e.g. aprons); barium sulfate is frequently used for this purpose in the state of the art. In addition, plastic blanks containing fillers have a larger surface, a fact that is advantageous in the coating of this invention (better dispersion).

The coating of plastics in the form of films, ribbons (a special kind of film), fibers or granules with one or more active substances in thin layers, preferably with layer thicknesses of between 10 and 100 nm, is possible in various ways using chemical and, above all, physical methods.

The following does not deal with these coating techniques as such but exemplarily only with the use of plastics coated by means of these techniques and it is specifically assumed that the coating takes place by means of physical methods.

All methods taken into account for the coating take place under vacuum and thus automatically involve drying of the plastic within the process step of coating, which drying satisfies all requirements mentioned in the following of the plastic prepared according to this invention in its being further processed.

Furthermore, to make things easier it is assumed that exclusively metals are used for the coating which are in an elementary state and that the metal layer that results from the coating process is generally very dense and therefore exhibits an impermeability to e.g. water vapor in time spans that are relevant for process-related considerations.

Due to the extraordinary importance of these materials for medical catheters, permanently thermoplastic polyurethane is a preferred plastic raw material. Mention be also made of novel plastics that are similar to common polyurethanes (e.g. "carbothanes").

For the use of other materials, however, the possibilities described in the following must be altered depending to the material used.

It is a particular property of polyurethanes as well as "carbothanes" to be rather hygroscopic. As a consequence, it must be taken into account that ignoring absorbed moisture in processing steps involving temperatures that are relatively high (for plastics) may lead to undesired side products which may reduce the quality of the product and, in medical terms, may even be harmful. Therefore, the plastic must by all means be prevented from being subjected to such processing steps involving temperatures that are relatively high (for plastics) while it has moisture incorporated.

The purpose of the process variants listed in the following is to bring the plastic containing active substance after the coating process into a form that makes it possible to further process it in mixers, kneaders, extruders or other machines to form intermediates and/or to make final processing possible in extruders, injection molding machines or in other equipment, such as (hot-) pressing.

In all of these machine types, however, the processing of the used permanently thermoplastic material takes place under the influence of temperatures that are relatively high for plastics. When feeding such machines, particularly extruders, this temperature effect must therefore be taken into account and it must be ensured that the plastic to be processed could accept no more moisture since the coating step, which usually takes place in vacuum, wherein this may sometimes be prevented just by the plastic being protected by the coating itself either largely (applies to double-sided coated plastic film, the wider, relative to their thickness, the better)

or completely (applies to plastic in the form of externally coated granules, in practice also applies to plastic fibers or ribbons)

or that after the coating step those portions of the plastic that have not been completely coated are protected against the entrance of moisture by special measures, i.e. the plastic is taken out of the coating equipment, transported, stored and transported to the extruder (packaging under exclusion of air or even under protective gas)

or that the plastic that has (or might have) accepted moisture is once again effectively dried before the extrusion step, preferably right at the extruder.

It should also be noted that in some cases it might be advisable to add uncoated film or fibers (also uncoated granules) to the coated plastic for processing in the extruder.

Of course, these must by all means also be dry when fed into the extruder, which must be ensured by appropriate measures.

To check for and/or provide for dryness is also very important before the next step that involves elevated temperatures, i.e. when coated plastic has been kneaded in the last processing step, i.e. it does already contain the active substance(s) but has not yet been resealed by another coating.

It is pointed out at this point that although drying the granules a second time at the extruder is relatively easy, drying fibers a second time is a little more difficult and drying film a second time directly at the extruder requires special equipment that is unlikely to be available.

Regarding feeding the extruders, which give the plastic its final shape, it will in the following be assumed that the mixing and kneading effect in the extruder the plastic is subjected to in the extrusion step causes the active substance (s) applied as (a) coating(s) to be completely homogenously worked into the plastic substance according to this invention, for which special screws might be necessary, the specially shaped segments of which are capable of finely tearing apart and dispersing the applied coating.

Principally, it does not matter whether the extruders are fed
- with (coated) granules or
- by means of special feeding equipment with (narrow) ribbons or
- with (wide) film and/or film packages that may be coated single-sided or double-sided, maybe even coated with and/or packed in several layers and can also contain uncoated (interfacial) films,
- or with fibers and/or fiber bundles comminuted or as a whole.

With respect to the injection molding machines, it is assumed that the feed screws frequently present in such machines generally do not supply the mixing and kneading effect that may be expected from extruders but that these machines must be fed with homogenously mixed granules or at least chopped material in order to achieve satisfactory results.

In injection molding machines and (hot-)presses, it will in general, but at least for permanently plastic materials (i.e. in particular for polyurethanes), be best to use finished mixed and kneaded plastic in the form of granules, which in turn, however, may accept moisture and thus, if it does not come from the previous processing steps completely protected against the absorption of moisture, must be re-dried immediately before being fed into the machine, most preferably on-line.

The following applies for the special case of the use of film as a raw material for the process of the invention: The surface of the active substance per volume unit plastic that is effective after further processing depends only on the obtained number of layers of active substance per thickness unit plastic after the coating step, i.e. it depends only on the thickness of the film and on whether the film is coated single- or double-sided. The thickness of the coating merely determines the supply of active substance, i.e. the time span how long the system remains effective.

Apart from the standard layer thickness, the chosen coating method and the parameters used therein, especially also the parameters used in the coating process for the pretreatment of the surface (e.g. in glimming or sputter etching), have considerable influence on whether a prepared layer is only seemingly (optically) or really impermeable to water vapor.

After all, it depends on these parameters which internal strength the layers exhibit, how they adhere to the plastic and, consequently, how well the layers can be dispersed in the entire volume of the plastic during the subsequent mixing and kneading steps of the system and which geometric shape these discrete particles dispersed in the plastic have, from which fact the elasticity and strength values of the plastic produced according to this invention result in comparison to the values of the starting plastic.

Uncoated interfacial film may be used to prevent direct contact of the coated surfaces. These uncoated interfacial films must, of course, be taken into account in the balance "coating layers per thickness unit plastic".

The use of uncoated interfacial film renders the issue of moisture absorbance important for the following process steps, which issue had been almost eliminated by the double-sided coating of the (hygroscopic) plastic film. However, the mass required for such interfacial films relative to the mass of the coated film is smaller by at least a factor of two. Still, the interfacial films too must be dried in some way before they are used, together with the coated plastic film, in a process involving temperatures that are relatively high (for plastics).

It is a matter of what possibilities are available and of technical and economical considerations whether one would rather accept and solve this additional problem of drying an interfacial film, which is uncoated and therefore susceptible to moisture, which problem is quantitatively speaking not so grave, or chose the advantages and disadvantages of double-sided coated films without any interfacial films, or be satisfied with only single-sided coated films to begin with.

One possibility of processing plastics in a dry state is that the coated film, which could at first simply be exposed to ambient air, is comminuted (chopped) together with this interfacial film and then the mixture is dried and stored in this condition but secured against the acceptance of moisture.

The chopped product would be rather suitable for being fed into processing machines with appropriate feeding equipment, e.g. "packing screws". However, in order to obtain highest quality end products, it will in general be better to first prepare granules as an intermediate from the dried chaff by means of an extruder or other machines suitable for granulating (pelletizing) permanently thermoplastic materials (e.g. Theysohn-Compounder, Drais-Gelimat, Pallmann-Plast-Agglomerator or Condux-Plastcopactor), which intermediate may then, just as is common, be used for being fed into any usual machine for producing end products.

These granules with uncoated surface, however, are hygroscopic.

Since the final processing again involves relatively high temperatures, it must usually be dried again before being fed into the final processing machine, which according to the state of the art is easily possible in this form of granules anyway, and is rather common in the case of hygroscopic plastics.

In the following, a variety of methods for the further processing of plastics coated with active substances is described. A distinction shall be made between different substrates, namely films, granules and fibers.

Films can be economically produced in large quantities in any desired width and, above all, in almost any desired strength. The latter possibility leads to a very wide variety of possible content of active substance surface per volume unit, which after all determines the effectiveness of the finished plastic. In view of the low costs per weight unit and the little time and/or energy required for the coating step, for which an advanced, highly automated technology is available in the field of film, the use of film as a raw material is always to be considered when average-sized active substance surfaces per volume unit plastic are to be produced. The problems of further processing the plastics are acceptable when the produced amount is high enough.

If only one active substance is used to coat the film, a differentiation can be made between the following embodiments:

(a) Single-sided coating of the film with only one active substance and further processing of the coated film stacked or rolled so that an active substance layer always lays on top of an uncoated surface, which is automatically the case when the film is rolled.

(b) Double-sided coating of the film with only one active substance; this process renders a second drying step before the film is further processed to produce the end product unnecessary when the process is carried out without major interruptions. This method, however, leads to a loss of active substance surface in the course of the further processing because it cannot be avoided that active substance surfaces are pressed onto one another during further processing.

(c) Double-sided coating of the film with only one active substance, wherein an uncoated interfacial film is used, which prevents the partial loss of active surface in the course of further processing in that active substance surfaces are not pressed directly onto one another; in contrast, due to this interfacial film an ion-conducting interfacial layer is formed.

If two different active substances are used to coat the film, a differentiation can be made between the following embodiments:

(a) Single-sided coating of the film:
   (i) Single-sided coating of the film with only one of the two active substances per film; these films are then mixed by stacking them, wherein the desired ratio of active surfaces of the two active substances can be achieved by the number of layers of accordingly coated films.
   (ii) Single-sided coating of the film with both active substances simultaneously in one layer. No true alloy-formation takes place. The desired ratio of the active substance concentrations can principally be adjusted by the ratio of the portion of each of the two active substance components in the coating. However, the ratio of ion release of the two active substances does not remain stable during the application.

(b) Double-sided coating of the film:
   (i) With only one of the two active substances on the upper and lower side of the same film; subsequently the films are mixed by stacking them, wherein the desired ratio of active surfaces of the two active substances can be adjusted by the number of correspondingly coated layers or the mixture takes place by chopping the film without using an uncoated interfacial film; if the process is carried out without major interruptions, this renders another drying step before further processing to obtain a finished product unnecessary. During further processing it cannot be avoided that the surfaces coated with both active substances are pressed directly onto one another, which in a later moist state causes the formation of local elements. This leads to ions of the less noble element preferably penetrating the surface during use of the plastic containing two active substances before a final state gradually stabilizes.
   (ii) Double-sided coating of the film with only one of the two active substances on each side of the film and subsequent mixing of the films by stacking them, wherein the desired ratio of the active surfaces of the two active substances can be adjusted by the number of the layers of the correspondingly coated films or by chopping them together with an uncoated interfacial film. The formation of local elements described above under item (i) and the thus given initially stronger release of ions of the less noble element does not take place because due to the uncoated interfacial film no layers of different active substances can be pressed together in the course of the further processing.
   (iii) Double-sided coating of the film with one of the two active substances on one side and the other active substance on the other side of the film and subsequent stacking or chopping without using an uncoated interfacial film; if the process is carried out without major interruptions, this renders another drying step before further processing to obtain a finished product unnecessary. During further processing it cannot be avoided that the surfaces coated with both active substances are pressed directly onto one another, which in a later moist state causes the formation of local elements. This leads to ions of the less noble element preferably penetrating the surface during use of the plastic containing two active substances before a final state gradually stabilizes.
   (iv) Double-sided coating of the film with one of the two active substances on one side and the other active substance on the other side of the film and subsequent stacking or chopping using an uncoated interfacial film: The formation of local elements described above under item (i) and the thus given initially stronger release of ions of the less noble element does not take place because due to the uncoated interfacial film no layers of different active substances can be pressed together in the course of the further processing.

When 3 or more active substances are used, the principles of the embodiments discussed for two active substances apply correspondingly.

Granules can be economically produced in large quantities; however, only in a rather restricted diameter range. The ratio of surface to volume is defined strictly (linear) dependent on the diameter of the granules. This property results in a very reduced possibility of variations for the content of active substance surface per volume unit, which after all determines the effectiveness of the finished plastic.

In view of the low costs per weight unit and the little time and/or energy involved in the coating step, wherein, above all, the technology of coating bulk material (e.g. of electric resistors) may be used (in the process of this invention a very uniform coating is of no importance), as well as the pleasant possibilities for further processing of the granules to obtain finished products, the use of granules as a raw material is always to be considered when small active substance surfaces per volume unit plastic are sufficient.

If only one active substance is used to coat the granules, a differentiation can be made between the following embodiments:

(a) The granules are coated once.
(b) The granules are coated twice with kneading and re-granulation inbetween; the specific active substance surface is twice that of only one coating step.
(c) The granules are coated x times with kneading and re-granulation inbetween every two coating steps; the specific active substance surface is x times that of only one coating step.

If two active substances are used to coat the plastic granules, a differentiation can be made between the following embodiments:

(a) Coating of separated granule amounts with one active substance each as described above and subsequent mixing of the granules coated with the different active substances in the desired ratio of the active substances.
(b) Simultaneous or sequential coating of the granules with different active substances. No real alloys are formed. The desired ratio of the various active substances can be adjusted by the ratio of the portion of each of the two active substance components of the coating. The ratio of the release of ions of these two active substances thus does not remain stable during application.
(c) Coating of granules first with one active substance according to the above-mentioned method, kneading, granulation and re-coating of the same granules according to the above method with the same or another active substance. The desired surface of each active substance per volume unit of the plastic and thus also the ratio of the two active substances can be adjusted by the number of coating processes followed by re-granulation.

When 3 or more active substances are used, the principles of the embodiments discussed for two active substances apply correspondingly.

Fibers can be produced somewhat economically in large quantities.

A rather extensive range of producible diameters is possible, in particular very small diameters. This fact in itself leads to a wide variety for the possible content of active substance surface per volume unit plastic, which after all determines the effectiveness of the finished plastic.

In view of the considerable manufacturing costs per weight unit and the considerable time and/or energy involved in the coating as well as the further processing, the use of fibers as a raw material is probably only considered when extremely large active substance surfaces per volume unit plastic are to be produced.

If one active substance is used to coat the fibers, a differentiation can be made between the following embodiments:

(a) When the fibers are coated once by means of water-vapor impermeable coating all around, re-drying before further processing and/or final processing is unnecessary; however, it leads to a loss of active substance surface (relative to the active surface in the end product expected by purely mathematic calculation) in the course of this further and/or final processing because active substance surfaces are inevitably pressed onto one another.

(b) The fibers are coated twice and kneaded and re-spun inbetween; the specific active substance surface is twice that of only one coating step.

(c) The fibers are coated x times and kneaded and re-spun inbetween every two coating steps; the specific active substance surface is x times that of only one coating step.

If two active substances are used to coat the fibers, a differentiation can be made between the following embodiments:

(a) Coating of separated fiber amounts with one active substance each as described above and subsequent mixing of the fibers coated with the different active substances in the desired ratio of the active substances.

(b) Simultaneous or sequential coating of the fibers with different active substances, wherein no real alloys are formed. The desired ratio of the various active substances can principally be adjusted by the ratio of the portion of each of the two active substance components of the coating. However, the ratio of the release of ions of these two active substances does not remain stable during application.

(c) Coating of the fibers first with one active substance according to the above-mentioned method, kneading, re-spinning and coating of these fibers according to the above method using the same or another active substance. The desired surface of each active substance per volume unit of the plastic and thus also the ratio of the two active substances can be adjusted by the number of coating processes followed by re-spinning.

When 3 or more active substances are used, the principles of the embodiments discussed for two active substances apply correspondingly.

Ribbons are a special kind of film. They can be produced economically in large quantities in any desired width and strength. The latter option leads to a very wide variety for the possible content of active substance surface per volume unit plastic, which after all determines the effectiveness of the finished plastic. In view of the low manufacturing costs per weight unit and the relatively little time and/or energy involved in the—also double-sided—coating of ribbons, for which the advanced, highly automated technology available for film can be employed, the use of ribbons as a raw material is always to be considered when average-sized active substance surfaces per volume unit plastic are to be produced. Ribbons can also be sufficiently coated on the narrow sides so that they can then be considered coated all around. Unlike wide films, ribbons can easily be fed into many extrusion machines without further pre-communition (and the usually following further intermediate steps), which leads to a decisive simplification of the entire manufacturing process of plastics of this invention but of course involves the use of higher amounts of active substance.

Double-sided coating of the film with only one active substance makes it possible to eliminate any re-drying steps before further processing and/or final processing when the coating is water-vapor impermeable all around, but it involves a loss of active substance surface in the end product in the course of the further and/or final processing because it cannot be avoided that active substance surfaces are pressed onto one another during further processing.

Another embodiment is characterized in that at first a coated plastic blank is produced according to one of the above-described methods but with a higher concentration of one or more antimicrobially active metal(s) and/or metal compound(s); this coated plastic blank is subsequently comminuted or molten down together with uncoated plastic blanks and is finally given the desired shape according to common methods. In this process the uncoated plastic blanks may be made of the same and/or other plastic(s) as the coated plastic blank.

EXAMPLE

Approx. 80 cm$^2$-large polyurethane films of 0.25 mm thickness were vapor-deposited with a silver layer of approx. 10 nm thickness in a high-vacuum system for antireflection coating of optical lenses. Under a light microscope the silver layer showed no inherent structure whatsoever, only the unevenness of the film could be seen as unevenness of the coating. Subsequently, the films were comminuted and molten down under stirring at approx. 240° C. Specimen (little platelets) were produced from this mass by means of hot-pressing.

The silver content of these specimen produced from the vapor-deposited silver films was determined upon reaction with nitric acid by means of the AAS method to be approx. 350 ppm, wherein, however, due to the imperfections of the preparation of the samples, considerable dispersion of the (three) measured values had to be accepted. Regarding the order of magnitude, this result is only 1/30 of the values stated as the minimum necessary for the effective use of silver powder in the state of the art.

These specimen proved to be fully antimicrobially effective against the colonisation by the bacterium staphylococcus epidermidis. This examination was carried out according to the method described in DE-C-42 26 810.

Test for Antimicrobial Effectiveness

The used plastic samples were produced by hand by means of melting and stirring under controlled thermal conditions.

In the cooling phase, each of the samples in the form of sheets having a diameter of 132 mm received 8 cup-shaped indentations having a volume of 0.5 ml each.

A total of nine different test sheets were produced from permanently thermoplastic polyurethane films "Platilon U 073", (polyether type) 0.18 mm thick that were coated with a) silver 10 nm single-sided,
b) silver 30 nm single-sided,
c) silver 60 nm single-sided,
d) silver 30 nm double-sided,
e) silver 30 nm on one side and silver 60 nm on the other side,
f) silver 30 nm on one side and copper 30 nm on the other side,
g) copper 30 nm double-sided, in a system actually designed for coating optical parts. For the purpose of checking test sheets a) and c) were produced twice.

For the purpose of comparison, two sheets were produced from uncoated film.

According to common gas sterilization of these sheets, the indentations were filled with physiological salt solution and inoculated in successive examination steps with the following germs in the stated concentrations:

*Staphylococcus epidermidis*: $5 \times 10^7$ germs/ml
*Staphylococcus aureus*: $5 \times 10^7$ germs/ml
*Streptococcus faecalis*: $5 \times 10^7$ germs/ml
*Escherichia coli*: $5 \times 10^7$ germs/ml
*Pseudomonas aeruginosa*: $5 \times 10^7$ germs/ml
*Candida albicans*: $5 \times 10^7$ germs/ml Upon such inoculation with germ suspension, the sheets were positioned in an incubator and kept there for 48 hours.

After about half an hour, the content of the cups is, judging by visual appearance, dried up.

After a total of 48 hours, the sheets were removed from the incubator and the cups were refilled with physiological salt solution. After another 15 minutes the newly formed suspension was removed and introduced into nutrient broth.

While all germ suspensions applied to the sheets of plastic in the starting condition immediately fully proliferated after this test, generally all tested germs had died on all plastic sheets treated according to the processes a) to f). Suspensions, in which some germs still proved to be able to multiply, were found only in those cups in which a visual examination clearly showed "blind spots", i.e. due to the imperfections of the stirring by hand no metal can be seen under the surface of these "blind spots". The presence of germs able to multiply is thus not due to the effect of the plastic of this invention but exclusively due to imperfections in producing it.

The performed tests in which no "blind spots" caused exceptional results, showed a 100% success.

This result confirms the thought underlying this invention that in addition to the choice of active substance and the choice of plastic, here mainly regarding its capability to accept water and make diffusion of metal ions possible, above all the ratio of active surface per volume unit plastic determine the effectiveness rather than the weight percentage of active substance in the plastic, particularly since in all examined cases this portion is by far less than what it should at least be for demonstrable effectiveness according to available patent publications.

We claim:

1. A method for producing antimicrobial plastic bodies, comprising the steps of:

a) providing a plastic blank for forming said plastic body;

b) providing antimicrobial particles of at least one antimicrobially active metal or metal compound;

c) coating the plastic blank with said antimicrobial particles by a chemical or physical method;

d) processing the coated blank by at least one of comminuting and melting down; and e) forming the processed blank into a desired shape, which is said plastic body, wherein the antimicrobial particles of metal or metal compound are embedded in the plastic in the form of discrete particles.

2. The method of claim 1, characterized in that the blank is present in the form of film.

3. The method of claim 1, characterized in that the blank is present in the form of granules.

4. The method of claim 1, characterized in that the blank is present in the form of fibers.

5. The method of any one of claim 1, characterized in that the blank is coated with one antimicrobially active metal or metal compound.

6. The method of any one of claim 1, characterized in that the blank is coated with at least two different antimicrobially active metals or metal compounds.

7. The method of claim 2, characterized in that the film is coated on one side.

8. The method of claim 2, characterized in that the film is coated on both sides.

9. The method of claim 7, characterized in that the film is coated with at least two antimicrobially active metals or metal compounds simultaneously on one side.

10. The method of claims 8, characterized in that an upper and a lower side of the film are coated with different antimicrobially active metals or metal compounds.

11. The method of claim 3, characterized in that the granules are coated at least twice.

12. The method of claim 3, characterized in that the same granules are coated simultaneously or sequentially with at least two different antimicrobially active metals or metal compounds.

13. The method of claim 4, characterized in that the fibers are coated at least twice.

14. The method of claim 4, characterized in that the same fibers are coated simultaneously or sequentially with at least two different antimicrobially active metals or metal compounds.

15. The method of claim 8, characterized in that the film coated on both sides is stacked or chopped for further processing using an uncoated interfacial film.

16. Plastic body obtainable according to the method of claim 1.

17. The method of claim 1 characterized in that the coating is carried out by a plasma-assisted method.

18. A method of producing plastic bodies, comprising the steps of coating a plastic blank with at least one antimicrobially active metal or metal compound by means of a chemical or physical method, processing the coated plastic blank by at least one of comminuting and melting down, and subsequently giving the plastic a desired shape, wherein a higher concentration than a desired end concentration of the at least one antimicrobially active metal or metal compound is coated on said blank, and wherein the step of processing the coated blank by at least one of comminuting and melting down is carried out together with at least one uncoated plastic blank before giving the plastic a desired shape.

* * * * *